(12) United States Patent
Nishimura

(10) Patent No.: US 6,653,631 B2
(45) Date of Patent: Nov. 25, 2003

(54) APPARATUS AND METHOD FOR DEFECT DETECTION USING CHARGED PARTICLE BEAM

(75) Inventor: Hiroshi Nishimura, Kawasaki (JP)

(73) Assignee: Nikon Corporation, Tokyo (JP)

(*) Notice: Subject to any disclaimer, the term of this patent is extended or adjusted under 35 U.S.C. 154(b) by 298 days.

(21) Appl. No.: 09/899,018

(22) Filed: Jul. 6, 2001

(65) Prior Publication Data
US 2002/0005484 A1 Jan. 17, 2002

(30) Foreign Application Priority Data
Jul. 14, 2000 (JP) .......................... 2000-215130

(51) Int. Cl.[7] .............................................. H01J 37/21
(52) U.S. Cl. .................... 250/310; 250/306; 250/307
(58) Field of Search ................................. 250/306, 310, 250/307, 492.1, 311

(56) References Cited

U.S. PATENT DOCUMENTS 6,521,891 B1 * 2/2003 Dotan et al. ................ 250/310

* cited by examiner

Primary Examiner—Huan Tran
(74) Attorney, Agent, or Firm—Oliff & Berridge, PLC

(57) ABSTRACT

A main control system 34 prepares, in advance, a voltage map showing the amount of focus deviation of a secondary electron beam B2 at a detection surface of an electron beam detector 30 corresponding with the amount of charge-up generated on a sample 4 upon irradiation with a primary electron beam B1, and stores this voltage map in a storage device 43. During an observation, the main control system 34 reads the voltage map stored in the storage device 43 and corrects the focal position of the secondary electron beam B2 by controlling either the voltage applied to the secondary optical system 20 or the voltage applied to the sample 4. As a result, focal position deviations resulting from charge-up generated on the sample being observed can be corrected without causing inconvenience to an operator.

11 Claims, 9 Drawing Sheets

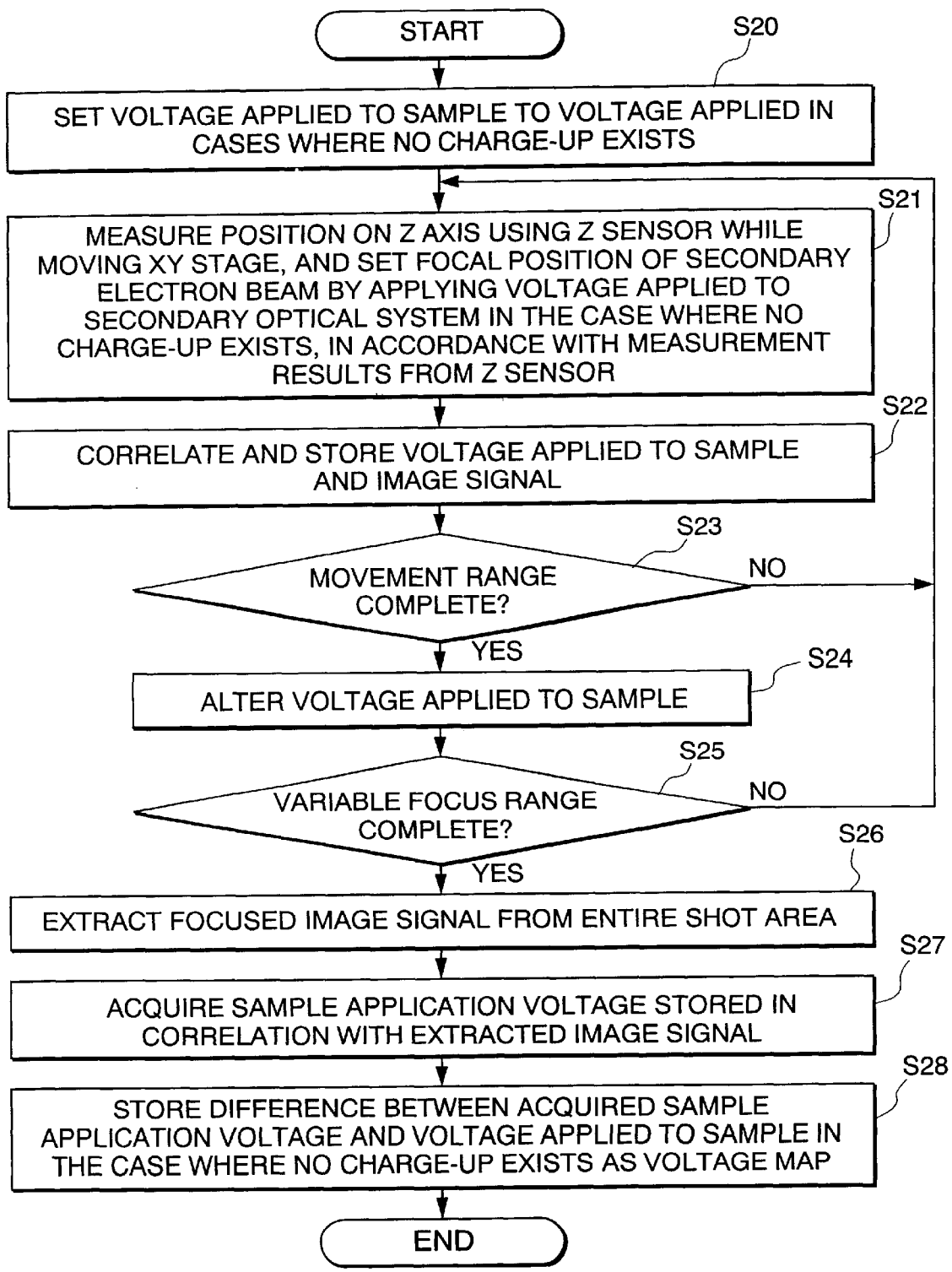

APPARATUS AND METHOD FOR DEFECT DETECTION USING CHARGED PARTICLE BEAM

BACKGROUND OF THE INVENTION

1. Field of the Invention

The present invention relates to an apparatus and a method for defect detection using a charged particle beam, and more particularly to a charged particle beam defect detection apparatus and a method of using such an apparatus in which a charged particle beam such as an electron beam or an ion beam is used for observing and detecting defects on the surface of an object such as a semiconductor substrate or a liquid crystal substrate.

2. Description of the Background Art

Semiconductor elements are formed by using planar techniques to generate a fine pattern on the surface of a semiconductor substrate. Demands for smaller semiconductor elements have lead to these patterns becoming finer and more highly integrated. Charged particle beam microscopes which utilize the charged particles from electron beams and the like are used for conducting observations and defect inspections of the surface condition of such semiconductor elements. Currently, the most widely known and widely used charged particle microscope is the scanning electron microscope (SEM). In recent years, imaging electron microscopes have been proposed as an alternative to scanning electron microscopes, and the development of charged particle beam imaging projection optical systems for this type of mapping electron microscopes is being actively pursued. As follows is a brief description of the construction of a charged particle beam imaging projection optical system.

A primary electron beam is emitted as an illuminating electron beam from an electron gun which functions as a charged particle source, and this beam passes through a primary optical system which functions as an illumination optical system, and enters an electromagnetic prism known as an E cross B (E×B). Passage through the E×B converts the cross-sectional shape of the primary electron beam to a linear shape, a rectangular shape, a circular shape or an oval shape, and the shaped beam then passes through a cathode lens which functions as an object optical system, and is illuminated onto the surface of a sample object. When the primary electron beam is irradiated onto the surface of an object, a reflected electron beam having a comparatively high energy is produced by reflection of the primary electron beam off the object surface, and furthermore, a secondary electron beam having a low energy is emitted from the object surface.

Of these two electron beams emitted from the object surface, the secondary electron beam is typically used for image generation. This secondary electron beam, which functions as an observation electron beam, passes through the cathode lens and enters the E×B. Following passage through the E×B, the secondary electron beam passes through a secondary optical system, which functions as an imaging optical system, and enters an electron beam detector. Observation and defect inspection of the object surface is then performed based on information obtained from injection of the secondary electron beam into the electron beam detector.

By the way, in devices such as the scanning electron microscope and the imaging electron microscope described above, where the observation and defect inspection of an object is carried out by the irradiation of charged particles such as an electron beam onto the object, because charged particles are irradiated onto the surface of the sample, the sample itself is charged up. Even if a charged particle beam with a uniform distribution relative to the sample surface is used, the amount of this charge-up will differ depending on the sample material. Therefore, in the case of a semiconductor element for example, the amount of charge-up in those areas where wiring is formed will differ from the amount of charge-up in those areas where an oxidation inhibiting film is formed, and so a charge-up distribution (a surface voltage distribution corresponding with the amount of accumulated charge on the object) generates.

Furthermore, the initial energy of a secondary electron beam generated in a section where charge-up has occurred will differ from the initial energy of a secondary electron beam generated in a section where absolutely no charge-up has occurred. Therefore, even if the focal position of the secondary optical system is adjusted so that the secondary electron beam from an area of no charge-up undergoes imaging onto the electron beam detector, the same focal position will not match the secondary electron beam emitted from an area where charge-up occurs. As a result, in order to ensure a more accurate observation of those areas where this charge-up phenomenon has occurred, the secondary optical system needs to be controlled and a correction made for this deviation in focal position. However, in order to correct this type of deviation in focal position, an operator must perform a manual correction for each sample, which is an extremely complex operation.

SUMMARY OF THE INVENTION

An object of the present invention is to provide a charged particle beam defect detection apparatus and a charged particle beam defect detection method, in which, even if charge-up occurs on the sample being observed, the focal position deviation resulting from this charge-up can be corrected without causing inconvenience to the operator, and a clear, in-focus observation and a highly accurate defect inspection can be performed.

In order to achieve the above object, a charged particle beam defect detection apparatus according to a first aspect of the present invention comprises an irradiation device which irradiates a beam from a charged particle beam source as a primary beam onto an object, an electron detection device which detects electrons emitted from the object as a result of the primary beam irradiation as a secondary beam and captures an image of the object, and a detection device which detects a surface voltage distribution for the object which corresponds with the amount of accumulated charge generated on the object upon irradiation with the primary beam.

According to this aspect of the invention, the surface voltage distribution for the object, corresponding with the amount of accumulated charge generated on the object upon irradiation with the primary beam, is detected with the detection device, and so information can be obtained which resolves the problems (such as focal position deviation and image distortion) due to accumulated charge on the object.

A charged particle beam defect detection apparatus according to a second aspect of the present invention comprises an irradiation device which irradiates a beam from a charged particle beam source as a primary beam onto an object, an electron detection device which detects electrons emitted from the object as a result of the primary beam irradiation as a secondary beam and captures an image of the object, a focus deviation detection device which detects in advance the degree of focus deviation of the secondary beam at the detection surface of the electron detection device, which corresponds with the amount of accumulated charge generated on the object upon irradiation with the primary beam, and a focus control device which controls the focal position of the secondary beam in accordance with the degree of focus deviation detected by the focus deviation detection device.

According to this aspect of the invention, the degree of focus deviation of the secondary beam at the detection surface corresponding with the amount of accumulated charge generated on the object upon irradiation with the primary beam, is detected in advance by the focus deviation detection device, and the focus control device then corrects the focal position of the secondary beam in accordance with this detected degree of focus deviation. Therefore, even in those cases where accumulated charge is generated on the object, the image of the object can be displayed in a focused state, and a clear and in-focus observation and a highly accurate defect inspection can be performed.

A charged particle beam defect detection apparatus according to a third aspect of the present invention is a charged particle beam defect detection apparatus according to the second aspect, in which a storage device is provided for storing the focus deviation values detected by the focus deviation detection device, and the aforementioned focus control device controls the focal position of the secondary beam based on the focus deviation values stored in the storage device.

According to this third aspect of the invention, the focus deviations values for the secondary electron beam resulting from accumulated charge on the object are stored in advance in the storage device, and during observation of the object, these deviation values are read from the storage device and used for controlling the focal position of the secondary beam. Therefore, in the case where, for example, the object is a semiconductor substrate with a plurality of shot areas with identical patterns set on the surface of the substrate, there is no necessity to detect the focus deviation of the secondary electron beam for each shot area, but rather the degree of focus deviation can be detected for just one of the shot areas. Furthermore, when observations are carried out for each of the shot areas, because the focal position can be controlled using the stored common focus deviation value, the throughput, namely the number of objects which can be observed within a unit of time, can be increased. Furthermore, in the case where a plurality of objects from an identical processing step, for example a plurality of substrates from a single lot, are subject to observation, then once again there is no necessity to detect the focus deviation for each object, and so the invention can also contribute to an increase in throughput in the case where observations should be performed for a plurality of objects.

A charged particle beam defect detection apparatus according to a fourth aspect of the present invention is a charged particle beam defect detection apparatus according to either one of the second aspect and the third aspect, in which a height detection device is provided for detecting the height of an object, and the aforementioned focus control device controls the focal position of the secondary beam based on both the aforementioned focus deviation values and the detection results from the height detection device.

According to this aspect of the invention, not only is the secondary electron beam focus deviation resulting from accumulated charge on the object corrected, but the height position of the object is also detected, and the thus detected height is also considered in controlling the focal position of the secondary beam. Therefore, even in those cases where, for example, the object is warped, the image of the object can be displayed in a focused state, and a clear and in-focus observation and a highly accurate defect inspection can be performed.

A charged particle beam defect detection apparatus according to a fifth aspect of the present invention is a charged particle beam defect detection apparatus according to the fourth aspect, in which the aforementioned storage device stores the object height values detected by the height detection device in correlation with the corresponding focus detection values, and the focus control device then controls the focal position of the secondary beam based on both the focus deviation values and the object height values correlated by the storage device.

According to this fifth aspect of the invention, the detected object height values and the detected focus deviation values are stored in a correlated manner, and when an observation is carried out, both these sets of stored data are used in controlling the focal position of the secondary beam. As a result, even if the object is warped, a clear, in-focus observation and a highly accurate defect inspection can be performed with a high level of throughput.

A charged particle beam defect detection apparatus according to a sixth aspect of the present invention is a charged particle beam defect detection apparatus according to any one of the second aspect through to the fifth aspect, wherein an imaging electron optical system is provided between the aforementioned electron detection device and the object, for imaging the secondary beam onto the detection surface of the electron detection device, and the aforementioned focus control device controls the focal position of the secondary beam by controlling the imaging electron optical system.

A charged particle beam defect detection apparatus according to a seventh aspect of the present invention is a charged particle beam defect detection apparatus according to any one of the second aspect through to the fifth aspect, in which a voltage application device is provided for applying a predetermined voltage to the object, and the aforementioned focus control device then controls the focal position of the secondary beam by controlling the voltage applied to the object via the voltage application device.

According to this aspect of the invention, the focal position of the secondary beam can be controlled without any complex control of the imaging electron optical system, simply by changing the voltage applied to the object, and so controlling the focal position of the secondary beam is simplified. As a result, not only can throughput be improved, but a clear, in-focus observation and a highly accurate defect inspection can be carried out with ease.

A charged particle beam defect detection apparatus according to an eighth aspect of the present invention is a charged particle beam defect detection apparatus according to the seventh aspect, in which the aforementioned focus control device controls the focal position of the secondary beam by controlling the voltage applied to the object based on the focus deviation values stored in the aforementioned storage device.

According to this eighth aspect of the invention, the focus deviations values for the secondary electron beam resulting from accumulated charge on the object are stored in advance in the storage device, and during observation of the object, these deviation values are read from the storage device and used for controlling the focal position of the secondary beam by controlling the voltage applied to the object. Therefore, in the same manner as the charged particle beam defect detection apparatus according to the third aspect, in the case where, for example, the object is a semiconductor substrate with a plurality of shot areas with identical patterns set on the surface of the substrate, there is no necessity to detect the focus deviation of the secondary electron beam for each shot area, but rather the degree of focus deviation can be detected for just one of the shot areas. Furthermore, when observations are carried out for each of the shot areas, because the focal position can be controlled using the stored common focus deviation value, the throughput, namely the number of objects which can be observed within a unit of time, can be increased. Furthermore, in the case where a plurality of objects from an identical processing step, for example a plurality of substrates from a single lot, are subject to observation, then once again there is no necessity to detect the focus deviation for each object, and so the invention can also contribute to an increase in throughput in the case where observations are to be performed for a plurality of objects.

A charged particle beam defect detection apparatus according to a ninth aspect of the present invention is a charged particle beam defect detection apparatus according to either one of the second and the third aspects, further comprising a height detection device which detects the height of the object, an imaging electron optical system provided between the aforementioned electron detection device and the object, for imaging the secondary beam onto the detection surface of the electron detection device, and a focused position calculation device which determines by simulation the relationship between the height of the object and the focused position of the imaging electron optical system relative to the detection surface of the aforementioned electron detection device in those cases where no accumulated charge exists on the object. The focus deviation detection device varies the focal position of the imaging electron optical system and saves the object height values detected by the height detection device together with the imaging results from the electron detection device, and then based on the difference between the focal position of the imaging electron optical system at the saved height value corresponding with the focused imaging result, and the focused position of the imaging electron optical system corresponding with the aforementioned height value as determined by the focused position calculation device, determines the degree of secondary beam focus deviation at the detection surface of the electron detection device which corresponds with the amount of accumulated charge.

A charged particle beam defect detection apparatus according to a tenth aspect of the present invention is a charged particle beam defect detection apparatus according to either one of the second and the first aspects, further comprising a voltage application device which applies a predetermined voltage to the object, a height detection device which detects the height of the object, an imaging electron optical system provided between the aforementioned electron detection device and the object, for imaging the secondary beam onto the detection surface of the electron detection device, and a focused position calculation device which determines by simulation the relationship between the height of the object and the focused position of the imaging electron optical system relative to the detection surface of the electron detection device in those cases where no accumulated charge exists on the object. The focus deviation detection device varies the voltage applied to the object via the voltage application device and saves the imaging results from the electron detection device when the focal position of the imaging electron optical system is matched with the focused position as determined by the focused position calculation device in accordance with the height values obtained by the height detection device, and then based on the amount of variation in the voltage applied to the body in the case where a focused imaging result is obtained, determines the degree of secondary beam focus deviation at the detection surface of the electron detection device which corresponds with the amount of accumulated charge.

According to these aspects of the invention, the height of the object is detected by the height detection device, and the height of the object is then taken into consideration in determining the degree of focus deviation resulting from accumulated charge on the object. Therefore, the construction of the charged particle beam defect detection apparatus can be simplified, and focus deviations resulting from variations in the height position of the object can be separated from focus deviations resulting from accumulated charge on the object even if the apparatus is not provided with a stage for varying the height position of the object. As a result, these aspects of the invention can be favorably applied to the correction of focus deviation resulting from accumulated charge even in those cases where the height of the object cannot be changed.

A charged particle beam defect detection method according to the present invention is a charged particle beam defect detection method for detecting defects in the surface of an object, by irradiating a beam from a charged particle beam source as a primary beam onto the object, detecting electrons emitted from the object as a secondary beam, and capturing an image of the object. The degree of focus deviation of the secondary beam which corresponds with the amount of accumulated charge generated on the object upon irradiation with the primary beam is detected in advance, and the focal position of the secondary electron beam is then controlled in accordance with this detected degree of focus deviation.

According to this charged particle beam defect detection method of the present invention, the same effects can be achieved as those described for the charged particle beam defect detection apparatus of the present invention.

BRIEF DESCRIPTION OF THE DRAWINGS

FIG. 10 is a flowchart showing a third method of preparing a voltage map.

DETAILED DESCRIPTION OF THE PREFERRED EMBODIMENTS

Figure 1:
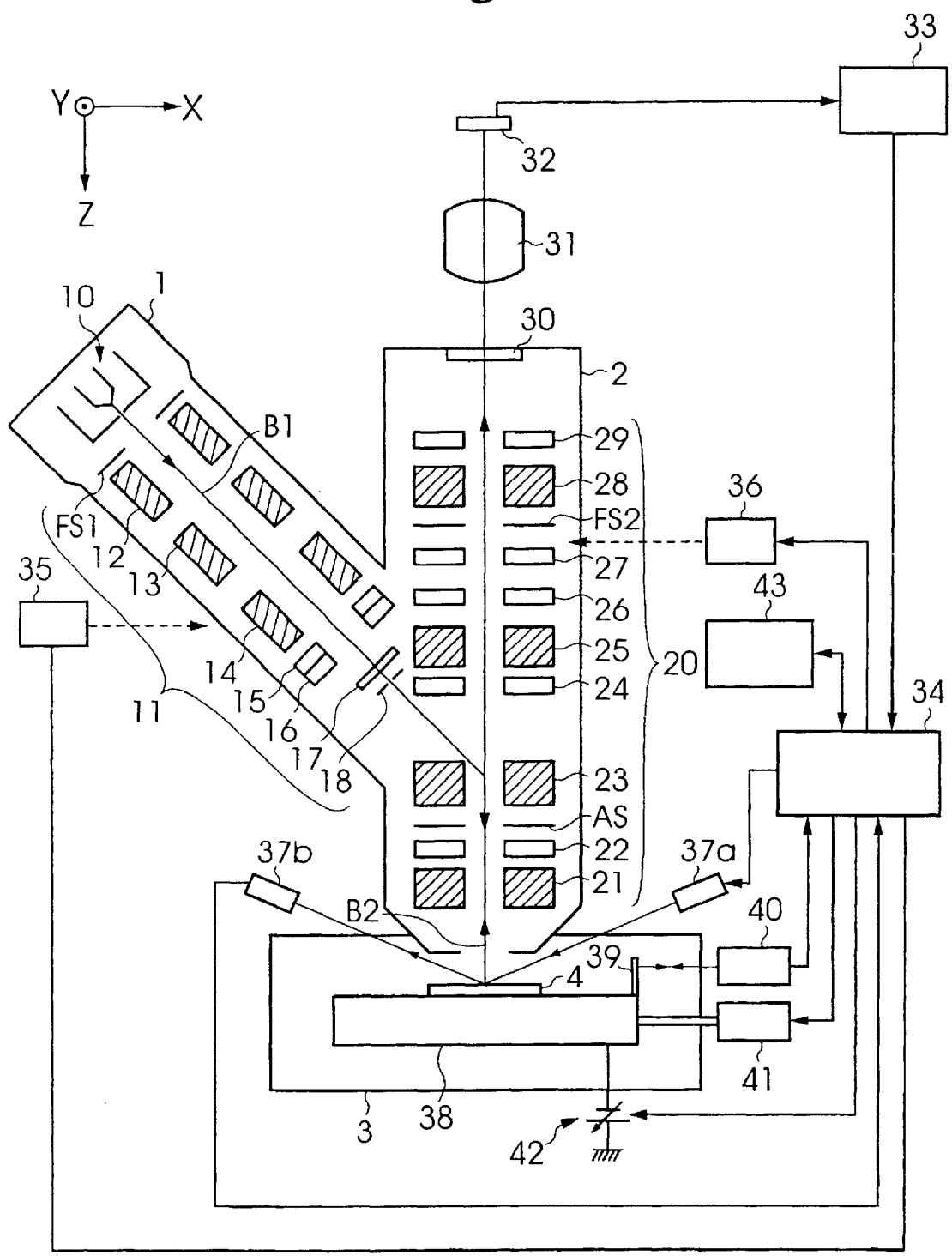
FIG. 1 is a diagram showing the construction of a charged particle beam defect detection apparatus according to an embodiment of the present invention.

A charged particle beam defect detection apparatus according to an embodiment of the present invention will be explained in detail with reference to the appended drawings. FIG. 1 is a diagram showing the construction of a charged particle beam defect detection apparatus according to the embodiment of the present invention. In the following description, XYZ orthogonal coordinates are set as shown in FIG. 1, and the positional relationships of each member are then described with reference to this XYZ orthogonal coordinate system. In the XYZ orthogonal coordinate system shown in FIG. 1, the XY plane is set across the object surface of the sample, and a normal line to the object surface of the sample is set as the Z axis. In the XYZ orthogonal coordinate system of FIG. 1, the XY plane is actually a horizontal plane, and the Z axis is set along the vertical.

The charged particle beam defect detection apparatus of this embodiment comprises mainly a primary column 1 which accelerates an electron beam and guides the beam onto a sample, a secondary column 2 which focuses a secondary electron beam generated when the electron beam is irradiated onto the sample onto the detection surface of an electron beam detector 30, and a chamber 3 which houses a sample 4 to be observed. The optical axis of the primary column 1 is set at an oblique angle relative to the Z axis, whereas the optical axis of the secondary column 2 is set substantially parallel with the Z axis. As a result, a primary electron beam B1 enters the secondary column 2 from the primary column 1 at an oblique angle. The primary column 1, the secondary column 2 and the chamber 3 are connected to an evacuation system (not shown in the drawing), and are evacuated using a vacuum pump, such as a turbo pump, provided within the evacuation system, so that the inside of the two columns and the chamber are maintained in a state of vacuum.

A thermionic emission electron gun 10 is provided inside the primary column 1, and a primary optical system 11 is positioned on the optical axis of the primary electron beam B1 irradiated from the thermionic emission electron gun 10. The chip of the thermionic emission electron gun 10 should preferably utilize a rectangular cathode of a material such as lanthanum hexaboride ($LaB_6$) which is capable of extracting a large current. The primary optical system 11 comprises a field stop FS1, irradiation lenses 12, 13, 14, aligners 15, 16, a scan aligner 17 and an aperture 18. The irradiation lenses 12, 13, 14 are electron lenses which utilize circular lenses, 4-pole lenses, or 8-pole lenses or the like. The convergence characteristics of the irradiation lenses 12, 13, 14 of the primary optical system 11 relative to the primary electron beam B1 are varied by varying the applied voltage. The irradiation lenses 12, 13, 14 may also be lenses which are symmetrical about the rotational axis, known as unipotential lenses or Einzel lenses.

A secondary optical system 20 is positioned inside the secondary column 2. The secondary optical system 20 is used for converging a secondary electron beam B2 produced when the primary electron beam B1 is irradiated onto a sample 4, and then imaging this secondary electron beam B2 onto the detection surface of the electron beam detector 30. The secondary optical system 20 comprises, in sequence along the Z axis from the sample 4, a cathode lens 21, a first aligner 22, an aperture stop AS, an E×B 23, a stigmeter 24, front imaging lenses 25, a second aligner 26, a stigmeter 27, a field stop FS2, rear imaging lenses 28, and a third aligner 29.

The field stop FS2 of the secondary optical system 20 is set with a conjugate positional relationship with the object surface of the sample 4, relative to the cathode lens 21 and the front imaging lenses 25. Furthermore, the front imaging lenses 25 and the rear imaging lenses 28 of the secondary optical system 20 are electron lenses which utilize circular lenses, 4-pole lenses, or 8-pole lenses or the like. The cathode lens 21, the front imaging lenses 25 and the rear imaging lenses 28 may also be lenses which are symmetrical about the rotational axis, known as unipotential lenses or Einzel lenses. The convergence characteristics of the cathode lens 21, the front imaging lenses 25 and the rear imaging lenses 28 of the secondary optical system 20 relative to the secondary electron beam B2, namely the focal position of the secondary electron beam B2, can be varied by varying the applied voltage. Furthermore, the deflection characteristics and the convergence characteristics of the E×B 23 relative to the primary electron beam B1 and the secondary electron beam B2 can be varied by varying either the applied voltage or the current.

The electron beam detector 30 is positioned at the direction −Z from the third aligner 29 of the secondary optical system 20. The secondary electron beam B2 generated when the primary electron beam B1 is irradiated onto the sample 4 is imaged onto the detection surface of the electron beam detector 30 by the secondary optical system 20. The electron beam detector 30 comprises an MCP (micro channel plate) for amplifying the electrons, a fluorescent screen for converting the electrons to light, and a vacuum window for enabling the light converted by the fluorescent screen to be emitted outside the secondary column 2 which is maintained in a vacuum condition. The light emitted from the electron beam detector 30, namely the optical image of the sample 4, passes through a relay lens 31 and enters an imaging element 32 such as a CCD (charge coupled device). The imaging element 32 converts the light irradiated onto an imaging surface into an electric signal, and outputs an image signal. A control unit 33 is connected to the imaging element 32. This control unit 33 reads the image signals output from the imaging element 32 in a serial manner, and outputs these signals sequentially to a main control system 34.

The main control system 34 performs image processing such as template matching on the image signals output by the control unit 33, and determines the existence of defects on the sample 4. Furthermore, the main control system 34 also outputs control signals to a primary optical system control section 35 and a secondary optical system control section 36 for controlling the optical characteristics of the primary optical system 11 and the secondary optical system 20 as well as the electromagnetic field of the E×B 23. By displaying the image signals output from the control unit 33 to the main control system 34 on a display device such as a CRT (cathode ray tube), an image of the sample 4 can be displayed on the display device. In addition, the main control system 34 also outputs a control signal to a Z sensor comprising a light transmission system 37a and a light reception system 37b, thereby measuring the positional coordinate along the Z axis of the sample 4. The main control system 34 also indirectly measures the amount of charge up on the sample 4 (the surface voltage distribution of the sample corresponding with the amount of accumulated charge on the sample). As follows is a description of the construction of the Z sensor which comprises the light transmission system 37a and the light reception system 37b. The Z sensor of the charged particle beam defect detection apparatus of this embodiment is a device which detects the position of the sample 4 along the Z axis by irradiating an illuminating light beam onto the sample 4 at an oblique angle.

Figure 2:
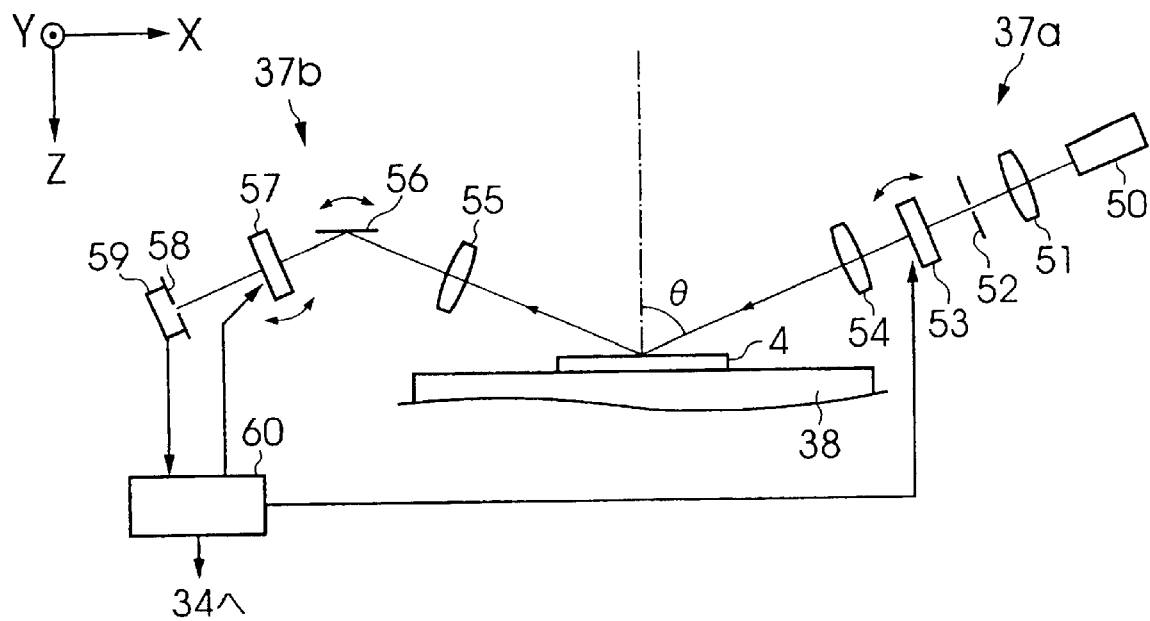
FIG. 2 is a side view showing the construction of a Z sensor of a charged particle beam defect detection apparatus according to the embodiment of the present invention.

FIG. 2 is a side view showing the construction of a Z sensor of the charged particle beam defect detection apparatus according to the embodiment of the present invention. As shown in FIG. 2, the light transmission system 37a comprises a light source 50, an illumination lens 51, a light transmission slit 52, a plane parallel plate 53, and a projection lens 54. The light reception system 37b comprises a condenser lens 55, a vibration mirror 56, a plane parallel plate 57, a light reception slit 58 and a silicon photodiode 59. In FIG. 2, an illuminating light beam emitted from the light source 50 passes through the illumination lens 51 and illuminates the light transmission slit 52. The light which passes through the light transmission slit 52 passes sequentially through the plane parallel plate 53 and the projection lens 54 and then illuminates the sample 4 from an oblique angle through a vacuum window (not shown in the figure), forming a slit image of the light transmission slit 52. The plane parallel plate 53 is able to be freely rotated about a rotational axis parallel with the Y axis of FIG. 2, and is positioned so as to enable shifting of the direction of the illuminating light beam emitted from the light source 50. The rotation angle of the plane parallel plate 53, namely the degree of shift of the illuminating light beam is controlled by a control section 60. The incident angle θ of the illuminating light beam irradiated onto the sample 4 is preferably set to a value of no less than 70 degrees so that the object surface of the sample 4 is detected with certainty and the detection sensitivity can be improved.

Reflected light from the surface of the sample 4 passes through a vacuum window (not shown in the figure) and is condensed by the condenser lens 55, then, the reflected light is irradiated onto the vibration mirror 56. The vibration mirror 56 vibrates with a constant vibration period about a central axis parallel with the Y axis shown in the figure. The light reflected off the vibration mirror 56 passes through the plane parallel plate 57 and reaches the light reception slit 58. Only the light which passes through the light reception slit 58 enters the silicon photodiode 59, which then detects the quantity of light. The detection result from the silicon photodiode 59 is output to the control section 60, and the degree of displacement of the sample 4 along the Z axis is determined. This degree of displacement is then output to the main control system 34 shown in FIG. 1. In the same manner as the plane parallel plate 53, the plane parallel plate 57 is able to be freely rotated about a rotational axis parallel with the Y axis shown in the figure, and is positioned so as to enable shifting of the direction of the reflected light reflected off the sample 4. The degree of this shift is controlled by the control section 60.

Figure 3:
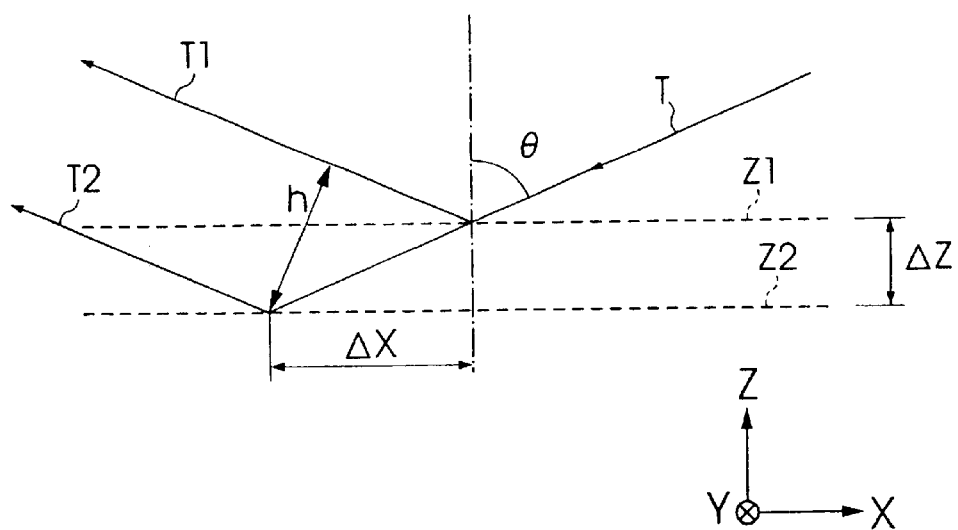
FIG. 3 is a diagram describing the measurement principles of the Z sensor.

As follows is a description of the measurement principles for a Z sensor of the above construction. FIG. 3 is a diagram describing the measurement principles of the Z sensor. If the current position of the object surface of the sample 4 is assumed to be at a position Z1 shown in FIG. 3, then an illuminating light beam T irradiated onto the sample surface at an incident angle θ is reflected off the object surface and becomes a reflected light beam T1. If the Z position of the sample 4 is then displaced by an amount ΔZ and the position of the object surface shifted to a position Z2 in FIG. 3, then the light reflected off the object surface of the sample 4 will now become the reflected light beam T2. At this point, the position of the slit image formed by the light transmission slit 52 will shift by an amount ΔX, and the reflected light beam T2 will display a sideways displacement h relative to the reflected light beam T1. This sideways displacement h can be determined geometrically, as shown by the formula (1) below.

$$h = 2 \cdot \Delta Z \cdot \sin \theta \quad (1)$$

As is evident from the formula (1) above, the displacement ΔZ of the sample 4 in the Z direction can be determined by measuring the displacement h. As described above, when the paths of the illuminating light beam and the reflected light beam from the surface of the sample 4 are shifted by rotating the plane parallel plates 53, 57, the position of the sample 4 along the Z axis, as detected by the silicon photodiode 59, will vary. Therefore, by controlling the rotation of the plane parallel plates 53, 57 so that the following two equations (2), (3) are satisfied, the position of the sample 4 along the Z axis can be measured without any displacement ΔX in the detection position of the slit image of the light transmission slit 52, even if the sample 4 is displaced along the Z axis.

$$h/2 = h1 \cdot M1 \quad (2)$$

$$h/2 = h2 \cdot M2 \quad (3)$$

In the formulae, h1 represents the amount of parallel shift in the illuminating light beam resulting from rotation of the plane parallel plate 53 of the projection optical system; h2 represents the amount of parallel shift in the reflected light beam resulting from rotation of the plane parallel plate 57 of the condensing optical system; M1 represents the inverse of the magnification of the optical system from the light transmission slit 52 to the sample 4; and M2 represents the inverse of the magnification of the optical system from the sample 4 to the light reception slit 58. The value h/2 shown in the above formulae (2), (3) is the condition for simultaneous rotation of the two plane parallel plates 53, 57 so that the position on the sample 4 of the slit image of the light transmission slit 52 does not fluctuate.

As described above, the silicon photodiode 59 detects a signal determined by the rotational angle of the vibration mirror 56 and the slit width of the light reception slit 58, in other words a signal based on the principles of a photoelectric microscope. Based on this detected signal, the sideways displacement of the light on the light reception slit 58 is then determined by the control section 60. Then, the degree of shift in the case when the plane parallel plates 53, 57 are positioned at a certain angle is subtracted from this determined displacement, and the magnification M2 of the condenser lens 55 also taken into account, to detect the position along the Z axis of the sample 4. The degree of displacement in the Z direction of the sample 4 due to the rotation of the plane parallel plates 53, 57 is then determined by the control section 60, and this degree of displacement is then added to the displacement value determined previously by the silicon photodiode 59, to calculate the final displacement of the sample 4 in the Z direction. This calculated displacement value is output to the main control system 34 of FIG. 1, where processing is carried out for adjusting the position of the sample 4 along the Z axis.

Returning to FIG. 1, numeral 42 represents a variable power supply for setting a negative voltage at the sample 4, where the set voltage on the sample 4 is controlled by the main control system 34. Setting the sample 4 at a negative voltage ensures that the secondary electron beam B2 emitted when the primary electron beam B1 is irradiated onto the sample 4 is accelerated towards the cathode lens 21, in other words, in the −Z direction. A storage device 43 is connected to the main control system 34. This storage device 43 stores the focal position for the secondary optical system 20, the Z axis positional information for the sample 4, the negative voltage set at the sample 4, and the image signals input from the imaging element 32, via the control unit 33, into the main control system 34.

Providing this storage device 43, means that even in those cases where charge-up occurs on the sample 4, the amount of correction required for the deviation in the focal position of the secondary electron beam B2 resulting from the charge-up can be determined, the secondary electron beam can be imaged onto the detection surface of the electron beam detector 30, and an image can be obtained which is sufficiently clear for detecting defects on the sample 4. As a result, in this embodiment, a map showing the deviation in focal position corresponding with charge-up (hereafter referred to as a voltage map) is prepared before the observation or defect detection is performed for the sample 4. Where possible, the voltage map should preferably store the focal position deviation amounts directly. However in the present embodiment, because the focal deviation is controlled by either the voltage applied to the secondary optical system 20, or the voltage applied to the sample 4, the voltage map stores those voltages necessary for adjusting the focal position. Methods of preparing this voltage map, and a description of the operations for correcting the focal position based on this voltage map are outlined below.

As follows is a description of the construction inside the chamber 3. An XY stage 38 onto which is mounted the sample 4 is positioned inside the chamber 3, and this XY stage 38 can move freely within the XY plane. An L shaped movable mirror 39 is attached to one end of the XY stage 38, and a laser interferometer 40 is positioned facing the mirror surface of the movable mirror 39. Although simplified in FIG. 1, the movable mirror 39 comprises a flat mirror with a reflective surface perpendicular to the X axis, and a flat mirror with a reflective surface perpendicular to the Y axis. Furthermore, the laser interferometer 40 comprises two X axis laser interferometers for irradiating a laser beam along the X axis onto the movable mirror 39, and a Y axis laser interferometer for irradiating a laser beam along the Y axis onto the movable mirror 39. One of the X axis laser interferometers and the Y axis laser interferometer are used for measuring the X coordinate and the Y coordinate for the XY stage 38. The difference between the measured values from the two X axis laser interferometers is used for measuring the rotational angle of the XY stage 38 within the XY plane.

Figure 4:
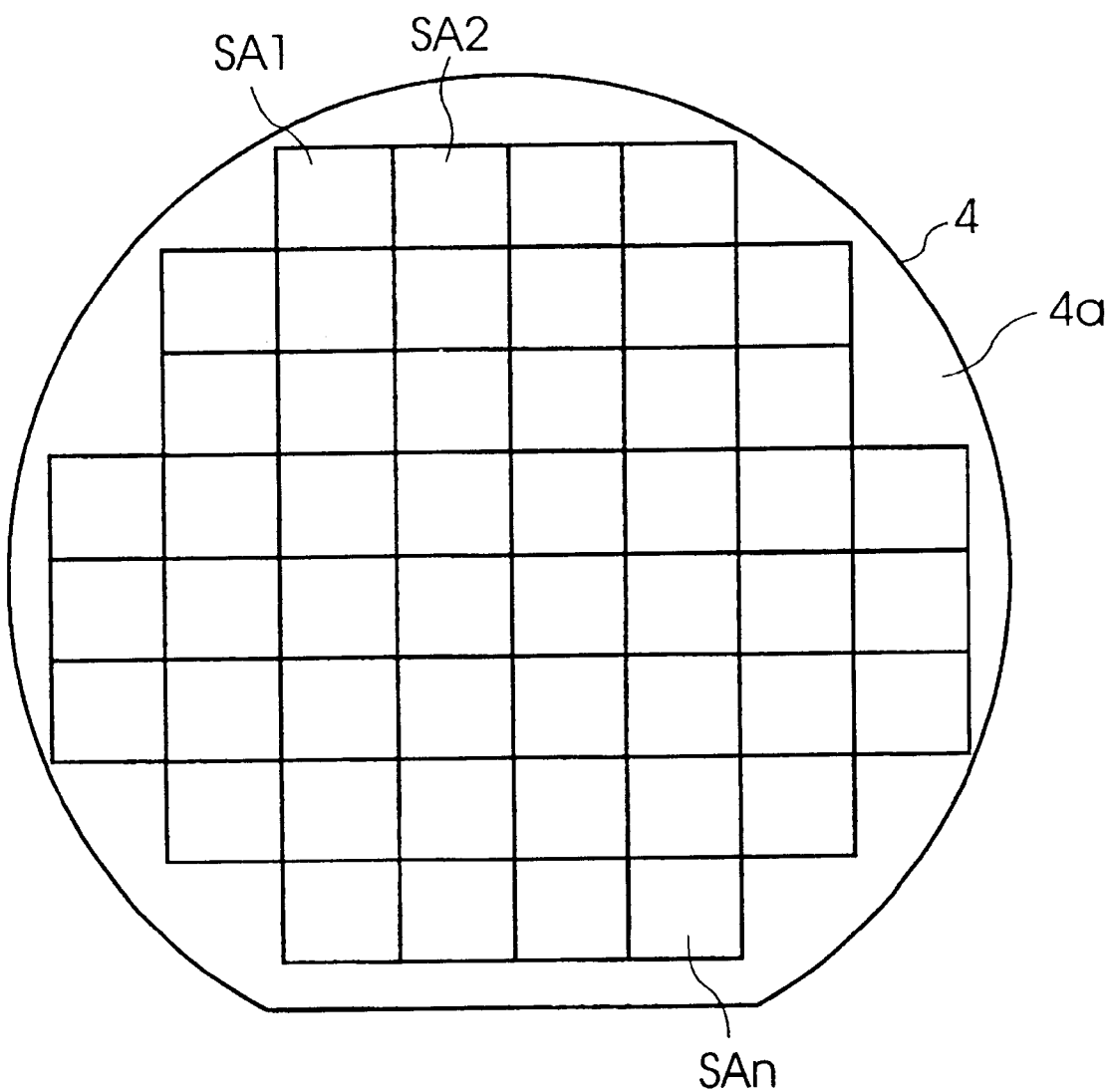
FIG. 4 is a top view showing one example of a sample.

The results of the measurements by the laser interferometer 40 are output to the main control system 34, and based on these results the main control system 34 outputs a control signal to a drive apparatus 41 for controlling the position of the XY stage 38 within the XY plane. Furthermore, although omitted from the figure, a Z stage which is capable of varying the position of the sample 4 along the Z axis, and a tilt stage for controlling the angle of the surface of the sample 4 relative to the XY plane, are also preferably provided in addition to the XY stage 38. In the present embodiment, in order to aid comprehension, the case is considered for a sample 4 shown in FIG. 4. FIG. 4 is a top view showing one example of the sample 4. The sample 4 shown in FIG. 4 is a semiconductor wafer in which a plurality of shot areas SA1, SA2, through to SAn (where n is a natural number) are set on the object surface 4a of the sample 4. An identical pattern is assumed to be formed on each of the shot areas SA1, SA2, through to SAn.

Figure 5:
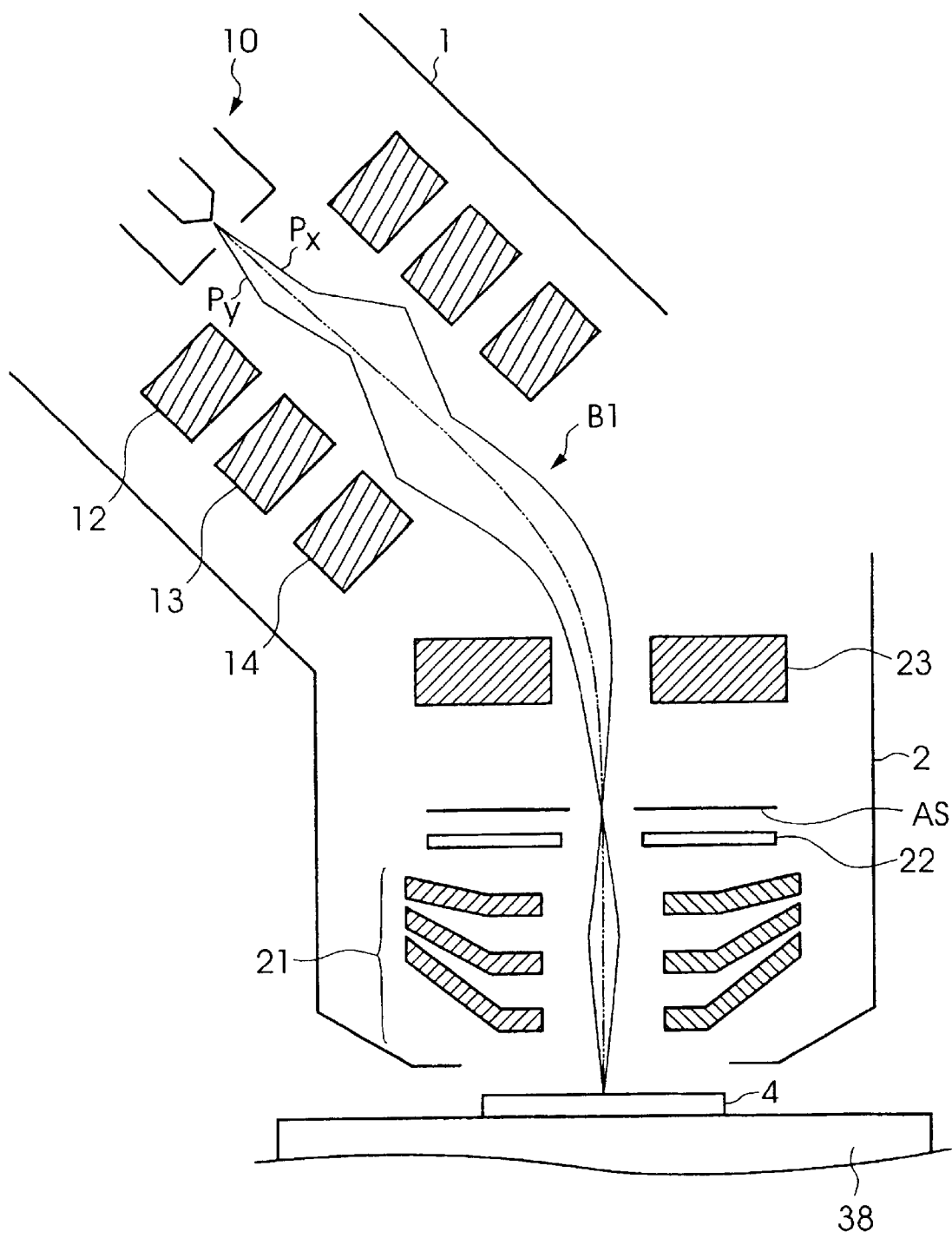
FIG. 5 is a diagram showing the trajectory of a primary electron beam of a charged particle beam defect detection apparatus according to the embodiment of the present invention.

The construction of a charged particle beam defect detection apparatus according to the embodiment of the present invention is described above. As follows is a detailed description of the trajectories of the primary electron beam B1 and the secondary electron beam B2 in a charged particle beam defect detection apparatus according to the embodiment of the present invention. FIG. 5 is a diagram showing the trajectory of the primary electron beam B1 of a charged particle beam defect detection apparatus according to the embodiment of the present invention. In FIG. 5, in order to ease comprehension, a portion of the elements of the primary optical system 11 are omitted. The primary electron beam B1 emitted from the thermionic emission electron gun 10 undergoes convergence and divergence under the influence of the electric fields formed by the irradiation lenses 12, 13, 14, as shown in FIG. 5. If the rectangular shaped chip of the thermionic emission electron gun 10 is set so that the longer axis lies along the X axis and the shorter axis lies along the Y axis, then the trajectory of electrons emitted in an X axis cross-section of the rectangular cathode are represented by a trajectory labeled $P_X$ in FIG. 5, and the trajectory of electrons emitted in a Y axis cross-section of the rectangular cathode are represented by a trajectory labeled $P_Y$ in FIG. 5.

Having been subjected to the influence of the irradiation lenses 12, 13, 14, the primary electron beam B1 enters the E×B 23 at an oblique angle. On entry into the E×B 23, the optical path of the primary electron beam B1 is deflected to a direction substantially parallel to the Z axis. The deflected primary electron beam B1 then reaches the aperture stop AS, and at this position, forms a crossover image of the thermionic emission electron gun 10. Following passage through the aperture stop AS, the primary electron beam B1 passes through the first aligner 22, is subjected to the lens action of the cathode lens 21, and Kohler-illuminates the sample 4.

Figure 6:
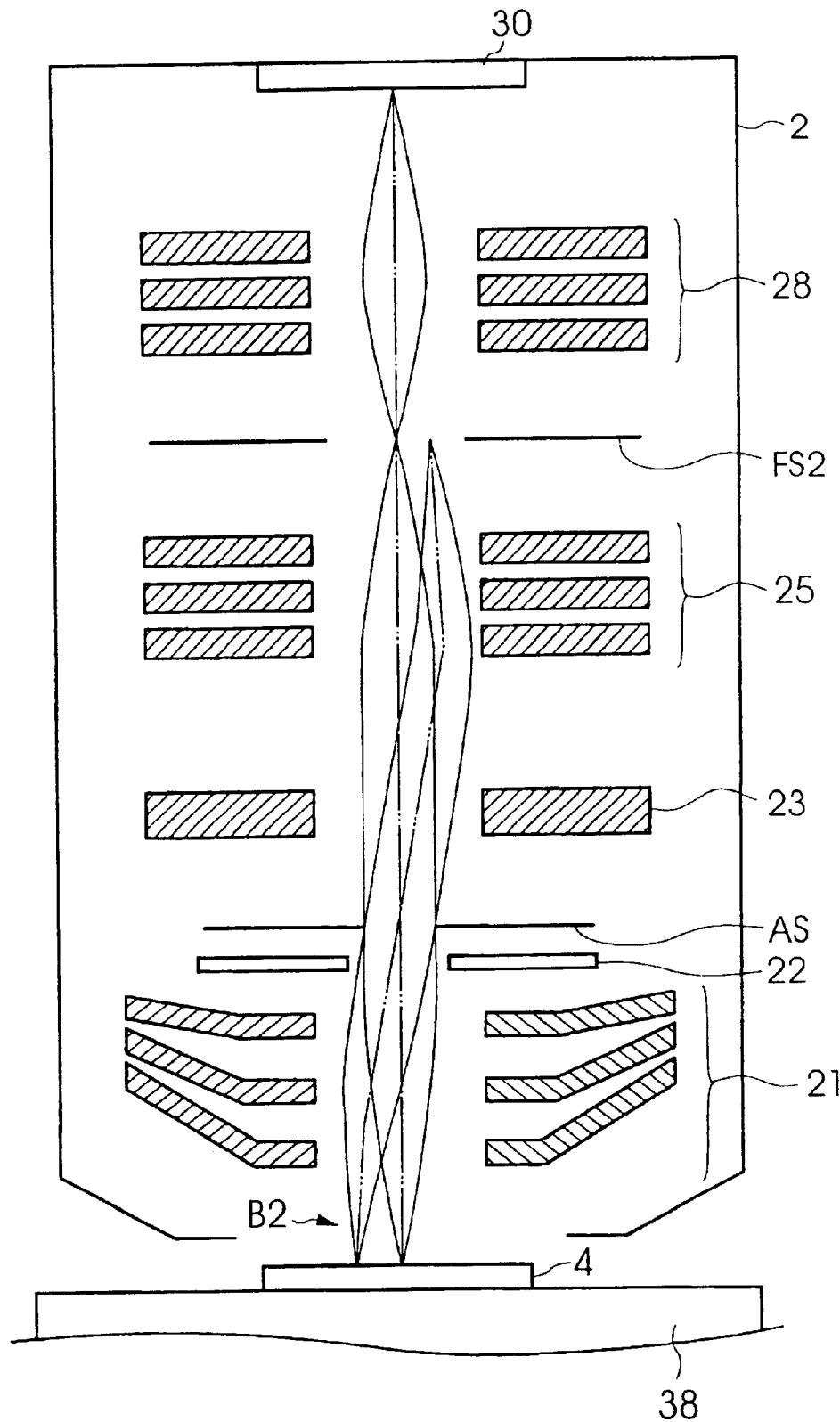
FIG. 6 is a diagram showing the trajectory of a secondary electron beam of a charged particle beam defect detection apparatus according to the embodiment of the present invention.

When the primary electron beam B1 is irradiated onto the sample 4, a secondary electron beam B2 and a reflected electron beam are generated at the surface of the sample 4, with a distribution corresponding to the surface shape of the sample 4, the material distribution within the sample 4, and variations in the potential on the surface. Of these two generated beams, the secondary electron beam B2 is generally the electron beam used for observation purposes. As described above, the initial energy of the secondary electron beam B2 is low, typically between 0.5 and 2 eV. As follows is a description of the trajectory of the secondary electron beam B2 generated from the sample 4. FIG. 6 is a diagram showing the trajectory of the secondary electron beam B2 of a charged particle beam defect detection apparatus according to the embodiment of the present invention. In FIG. 6, in order to ease comprehension, a portion of the elements of the secondary optical system 20 are omitted.

The secondary electron beam B2 emitted from the sample 4 passes sequentially through the cathode lens 21, the first aligner 22, the aperture stop AS and the E×B 23 of the secondary optical system 20. On passage through the E×B 23, the secondary electron beam B2 is converged by the front imaging lenses 25 and forms an image of the sample 4 at the location of the field stop FS2. Having passed through the field stop FS2, the secondary electron beam B2 undergoes a second convergence by the rear imaging lenses 28, and forms a magnified image of the object surface of the sample 4 on the detection surface of the electron beam detector 30.

Figure 7A:
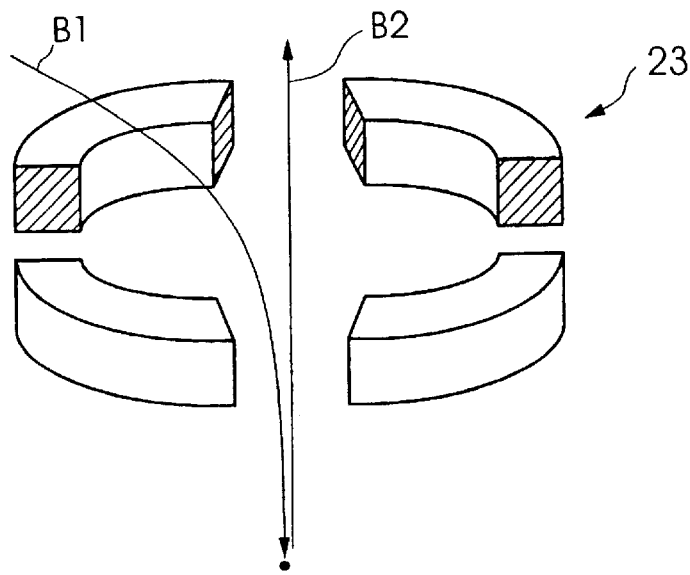
FIGS. 7A to 7C are diagrams describing the construction and operating principles of an ExB of a charged particle beam defect detection apparatus according to the embodiment of the present invention.
Figure 7B:
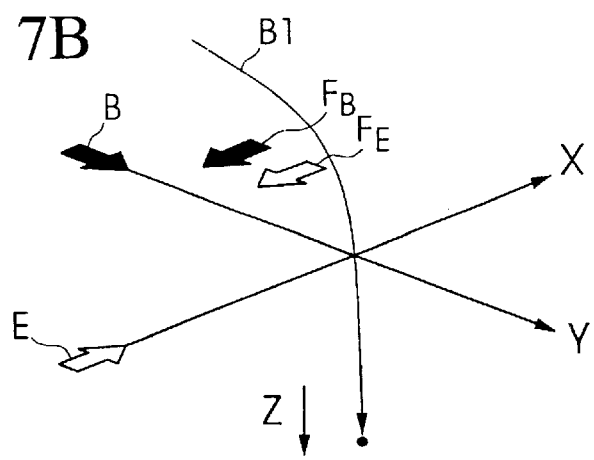
Figure 7C:
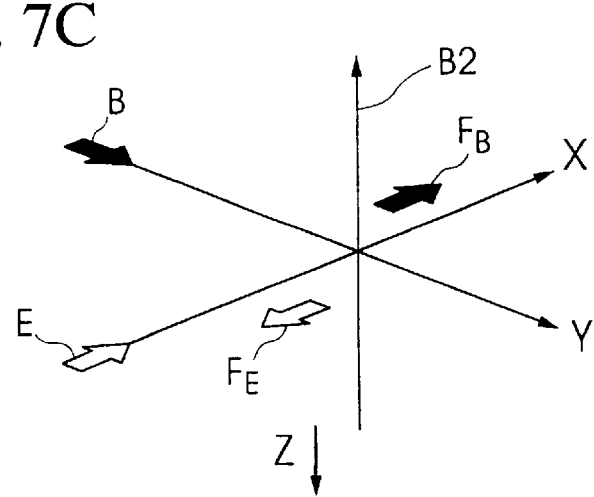

Next is a detailed description of the E×B 23 of a charged particle beam defect detection apparatus according to the embodiment of the present invention. FIGS. 7A to 7C are diagrams describing the construction and operating principles of an E×B 23 of a charged particle beam defect detection apparatus according to the embodiment of the present invention. FIG. 7A is a perspective diagram showing the construction of the E×B 23. As shown in FIG. 7A, the primary electron beam B1 emitted from the thermionic emission electron gun 10 is converged by the lens action of the primary optical system 11, and following entry into the E×B 23 undergoes a bending in trajectory (optical path) due to the deflection action of the E×B 23. The reason for this change in trajectory is that, as shown in FIG. 7B, when an electron beam of a charge q (the primary electron beam B1) passes through a mutually perpendicular electric field E and a magnetic field B with a velocity v in the +Z direction, the electron beam is acted upon by the resultant force of the force FE (=qE) due to the electric field and the force FB (=qvB) due to the magnetic field acting in the −X direction. As a result, the trajectory of the primary electron beam B1 is bent within the XY plane.

In contrast, the secondary electron beam B2 generated upon irradiation of the sample 4 with the primary electron beam B1 is subjected to the lens action of the cathode lens 21, passes through the aperture stop AS positioned at the focal position of the cathode lens 21, and enters and passes straight through the E×B 23. The reason for this direct passage through the E×B 23 is described below. As shown in FIG. 7C, when an electron beam of a charge q (the secondary electron beam B2) passes through a mutually perpendicular electric field E and magnetic field B with a velocity v in the −Z direction, the electron beam is acted upon by the resultant force of the force FE due to the electric field acting in the −X direction, and the force FB due to the magnetic field acting in the +X direction. At this point, the absolute values of the force FE due to the electric field and the force FB due to the magnetic field are set so as to be equal (E=vB), in other words so as to satisfy the Wien's condition. Therefore, the force FE due to the electric field and the force FB due to the magnetic field cancel one another out, the apparent force acting on the secondary electron beam B2 reduces to zero, and the secondary electron beam B2 passes straight through the E×B 23. As described above, the E×B 23 has a function for selecting the optical path of the passing electron beam, functioning as a so-called electromagnetic prism.

The construction of a charged particle beam defect detection apparatus according to the embodiment of the present invention has been described above, but as follows is a general description of the operations for adjusting the focal position of a charged particle beam defect detection apparatus of the embodiment of the present invention with the construction described above, with reference to FIG. 1. First, a sample 4 for observation is mounted onto a loader (not shown in the figure), and then transported into the chamber 3 on the loader. Having been transported into the chamber 3, the sample 4 is mounted onto the XY stage 38. Once the sample 4 has been mounted on the XY stage 38, the main control system 34 drives the XY stage 38 via the drive apparatus 41 and moves the sample 4 into the measurement range. Having completed the movement of the sample 4 within the XY plane, the main control system 34 sets the magnification of the secondary optical system 20, for example setting a low magnification to ensure a broad measurement range.

Having completed the above processing, the main control system 34 controls the Z sensor comprising the light transmission system 37a and the light reception system 37b, and measures the position of the sample 4 along the Z axis. Based on the measurement results from the Z sensor, the main control system 34 outputs a control signal to the secondary optical system control section 36 for adjusting the magnification of the secondary optical system 20, thereby setting the focal position of the secondary electron beam B2 emitted from the sample 4 at the detection surface of the electron beam detector 30. In other words, because the focal position of the secondary electron beam B2 varies in accordance with the position of the sample 4 on the Z axis, it is necessary to measure the position of the sample 4 on the Z axis using the Z sensor, and then adjust the magnification of the secondary optical system 20 accordingly.

Subsequently, the main control system 34 commences emission of electrons from the thermionic emission electron gun 10, irradiating the primary electron beam B1 via the primary optical system 11, the E×B 23, the aperture stop AS, the first aligner 22 and the cathode lens 21 onto the object surface of the sample 4, and then using the secondary optical system 20 to condense the secondary electron beam B2 generated at the object surface of the sample 4 and create an image on the detection surface of the electron beam detector 30. The light emitted from the electron beam detector 30, namely the optical image of the sample 4, passes through the relay lens 31 and undergoes photoelectric conversion to an image signal in the imaging element 32. This converted image signal is then input into the main control system 34 via the control unit 33. Based on the input image signal, the main control system 34 performs image processing such as template matching, and determines the existence of defects.

In those cases where the sample 4 is to be observed under magnification, the main control system 34 outputs a control signal to the secondary optical system control section 36 and raises the magnification of the secondary optical system 20. As before, at this point the main control system 34 adjusts the magnification of the secondary optical system 20 based on the measurement results from the Z sensor, thereby setting the focal position of the secondary electron beam B2 emitted from the sample 4 at the detection surface of the electron beam detector 30. Typically, any focal position deviation resulting from a deviation in the Z axis position of the sample 4 is corrected in this manner, prior to the observation and defect inspection being performed on the surface of the sample 4.

However, in those cases where charge-up occurs on the sample 4 as a result of irradiating the sample 4 with the primary electron beam B1, then because the initial energy of the secondary electron beam B2 emitted from the sample 4 is greater than the initial energy of the secondary electron beam B2 emitted from the sample 4 in those cases where charge-up does not occur, even if a deviation in focal position resulting from a deviation in the Z axis position of the sample 4 is corrected, the position of the image of the secondary electron beam B2, namely the focal position, will still be out of position. Therefore, in order to adjust this focal position deviation, the degree of deviation corresponding with the amount of charge-up on the sample 4 must be detected, and the focal position of the secondary electron beam B2 then adjusted by this degree of deviation.

Even if the focal position of the secondary electron beam B2 is altered by simply varying the voltages applied to the front imaging lenses 25 and the rear imaging lenses 28, because the initial energy of the secondary electron beam B2 emitted from the surface of the sample 4 is large, the Wien's condition cannot be satisfied within the E×B 23. Therefore, in those cases where charge-up occurs, in order to adjust the focal position of the secondary electron beam B2, the voltage and the current applied to the E×B 23 must be controlled so as to satisfy the Wien's condition. Therefore, in those cases where charge-up occurs on the sample 4, the main control system 34 must control the voltages applied to the front imaging lenses 25 and the rear imaging lenses 28, as well as the voltage and the current applied to the E×B 23, which is a complex control process.

In order to avoid this type of complex control, it is possible to omit the control of the voltage and the current applied to the E×B 23 for satisfying the Wien's condition, thereby simplifying the control process. Instead of controlling the voltage and the current applied to the E×B 23, it is also possible to satisfy the Wien's condition by controlling the variable power supply 42. In the case where the Wien's condition is satisfied by controlling the voltage and the current applied to the E×B 23, both the applied voltage and the current must be considered, but when the control of the variable power supply 42 is used to satisfy the Wien's condition, only the negative voltage set at the sample 4 need be considered, and so the control process can be simplified. Adjustment of the focal position of the secondary electron beam B2 may be performed via this simplified control process wherein only the negative voltage set at the sample 4 is considered, or may be performed by controlling the voltages applied to the front imaging lenses 25 and the rear imaging lenses 28, as well as the voltage and the current applied to the E×B 23.

In other words, by controlling the variable power supply 42 so that the initial energy value of the secondary electron beam B2 emitted from the sample 4 in those cases where charge-up occurs is the same as the initial energy value of the secondary electron beam B2 emitted from the sample 4 in those cases where charge-up does not occur, the Wien's condition can be satisfied in the E×B 23. By using the above control process, the initial energy value of the secondary electron beam B2 will be the same as the initial energy value of the secondary electron beam B2 emitted from the sample 4 in those cases where charge-up does not occur, and so the voltage applied to the front imaging lenses 25 and the rear imaging lenses 28 can be based solely on the measurement results from the Z sensor.

In order to adjust a deviation in the focal position of the secondary electron beam B2 corresponding with a charge-up amount, the amount of charge-up of the sample 4 and the degree of deviation in the focal position of the secondary electron beam B2 must first be determined. As a result, in the embodiment, before observation or defect detection can be performed on the sample 4, a voltage map showing the deviation in focal position of the secondary electron beam B2 corresponding with the amount of charge-up must first be prepared. The amount of charge-up will vary depending on the surface shape of the sample 4, the material distribution within the sample 4, and variations in the potential on the surface, although the voltage map may be prepared using an average charge-up value for the entire sample 4.

Furthermore, in the case of a sample 4 in which a plurality of shot areas SA1 to SAn are formed on the object surface 4a, as shown in FIG. 4, a voltage map may be prepared for one shot area (for example, the shot area SA1), and this voltage map then used for focal position adjustment during measurements of the other shot areas. Furthermore, in semiconductor element manufacture, a plurality of wafers are typically processed in a single lot. Therefore, the pre-prepared voltage map can be used for focal position adjustments during not only measurements of a plurality of shot areas on a single wafer, but also during measurements of other wafers with the same pattern formed on the shot areas.

First Method of Preparing a Voltage Map

Figure 8:
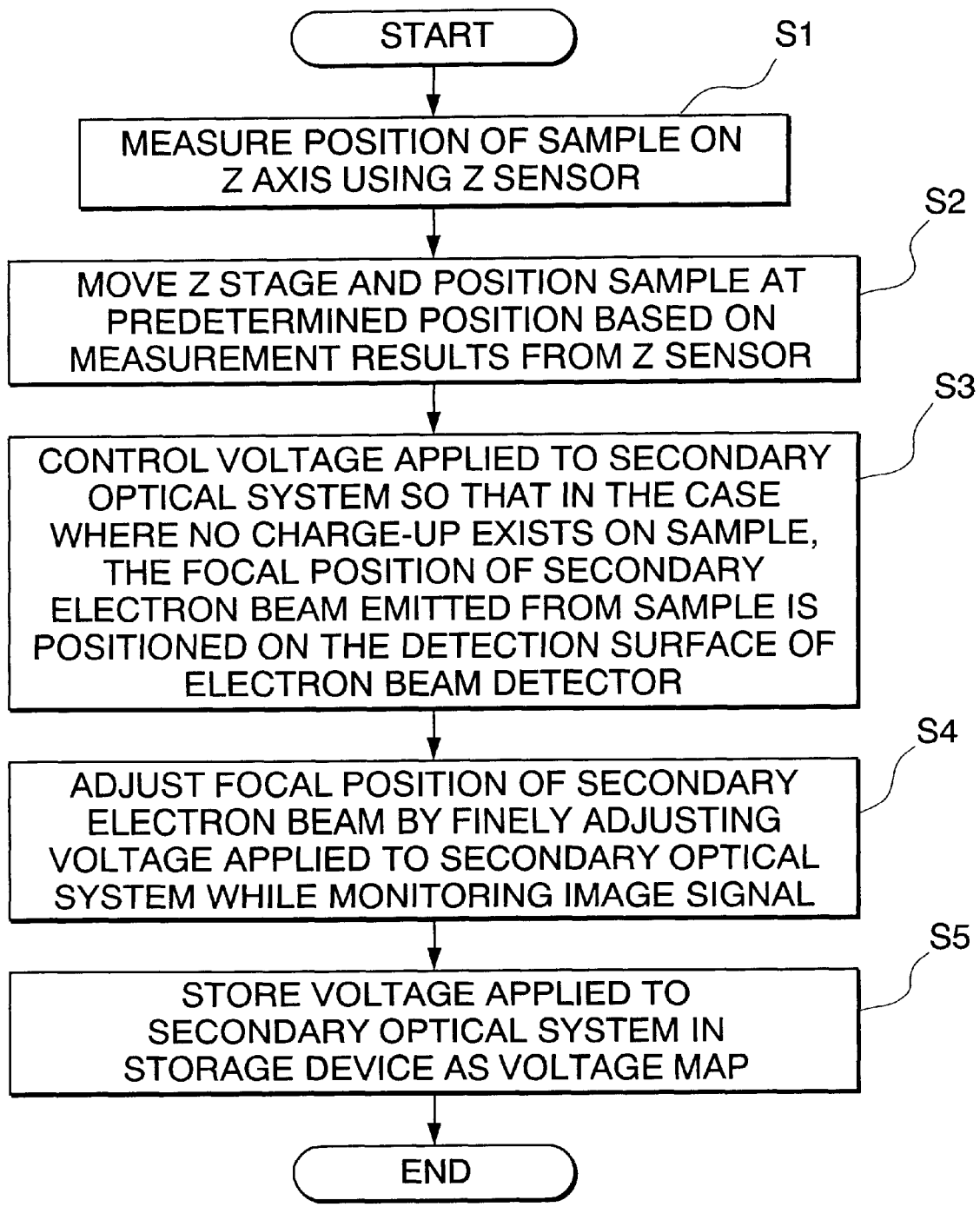
FIG. 8 is a flowchart showing a first method of preparing a voltage map.

As follows is a description of a method of preparing a voltage map. FIG. 8 is a flowchart showing a first method of preparing a voltage map. This first voltage map preparation method is a method of preparing a voltage map for those cases where the charged particle beam defect detection apparatus shown in FIG. 1 comprises a Z stage capable of moving the sample 4 in the direction of the Z axis. On commencement of the preparation, first the position of the sample 4 within the XY plane and the magnification of the secondary optical system 20 are set so that the measurement range falls within one shot area, and a predetermined negative voltage is then applied to the sample 4. The position of the sample 4 on the Z axis is then measured using the Z sensor comprising the light transmission system 37a and the light reception system 37b (step S1). Based on the measurement result, the main control system 34 then uses the drive apparatus 41 to drive the Z stage and position the sample 4 at a predetermined Z position (step S2). After positioning of the sample 4 at this predetermined Z position, if no charge-up exists on the sample 4, the main control system 34 adjusts the voltage applied to the secondary optical system 20 so that the secondary electron beam B2 emitted from the sample 4 is imaged onto the detection surface of the electron beam detector 30 (step S3).

In those cases where charge-up occurs on the sample 4, the focal position of the secondary electron beam B2 will be out of position even if the above adjustment is performed. Therefore, the image signal input from the imaging element 32, via the control unit 33, into the main control system 34 is monitored while the voltage applied to the secondary optical system 20 is finely adjusted, thereby adjusting the focal position of the secondary electron beam B2 (step S4). The voltage applied to the secondary optical system 20 in order to adjust the focal position of the secondary electron beam B2 will be the voltage map value at the Z position at which the sample 4 is positioned. The prepared voltage map is stored in the storage device 43 by the main control system 34 (step S5). By carrying out the processing outlined above, a voltage map can be prepared for the case where the charged particle beam defect detection apparatus shown in FIG. 1 comprises a Z stage capable of moving the sample 4 in the direction of the Z axis.

Second Method of Preparing a Voltage Map

The first method of preparing voltage map described above, is the method for the case where the charged particle beam defect detection apparatus comprises a Z stage and the voltage map preparation method related to those cases where the Z axis position of the sample 4 was able to be varied. However, because a stage such as the XY stage 38 on which the sample 4 is mounted is positioned inside the chamber 3, namely inside a vacuum, there are occasions where in order to simplify the construction inside the chamber 3, a Z stage is not provided. In such cases, if the levelness of the XY stage 38 is poor, or the sample 4 for observation is warped or bent, then simply moving the XY stage 38 within the XY plane is sufficient to vary the position of the sample 4 along the Z axis.

In such cases, the position of the sample 4 along the Z axis is first measured using the Z sensor comprising the light transmission system 37a and the light reception system 37b. Based on the results of this measurement, the main control system 34 then controls the voltage applied to the secondary optical system 20 and sets the focal position of the secondary electron beam B2 to a position corresponding with the position of the sample 4 along the Z axis. The voltage applied to the secondary optical system 20 in order to set the focal position of the secondary electron beam B2 is the voltage obtained by combining the voltage due to the positional deviation of the sample 4 along the Z axis, and the voltage due to charge-up.

Therefore, in the case where, for example, the focal positions of secondary electron beams B2 emitted from two samples at the same Z position but with different amounts of charge-up are both to be set at the detection surface of the electron beam detector 30, then the voltage applied to the secondary optical system 20 needs to be separated into the voltage due to the deviation of the sample 4 along the Z axis, and the voltage due to the charge-up. In other words, if a voltage map is prepared using the combined voltages, then the voltage map has no use in performing focal position corrections corresponding with the amount of charge-up, and unless a voltage map is prepared in which these voltages are separated out, adjustments of the focal position in accordance with a charge-up amount cannot be performed.

Figure 9:
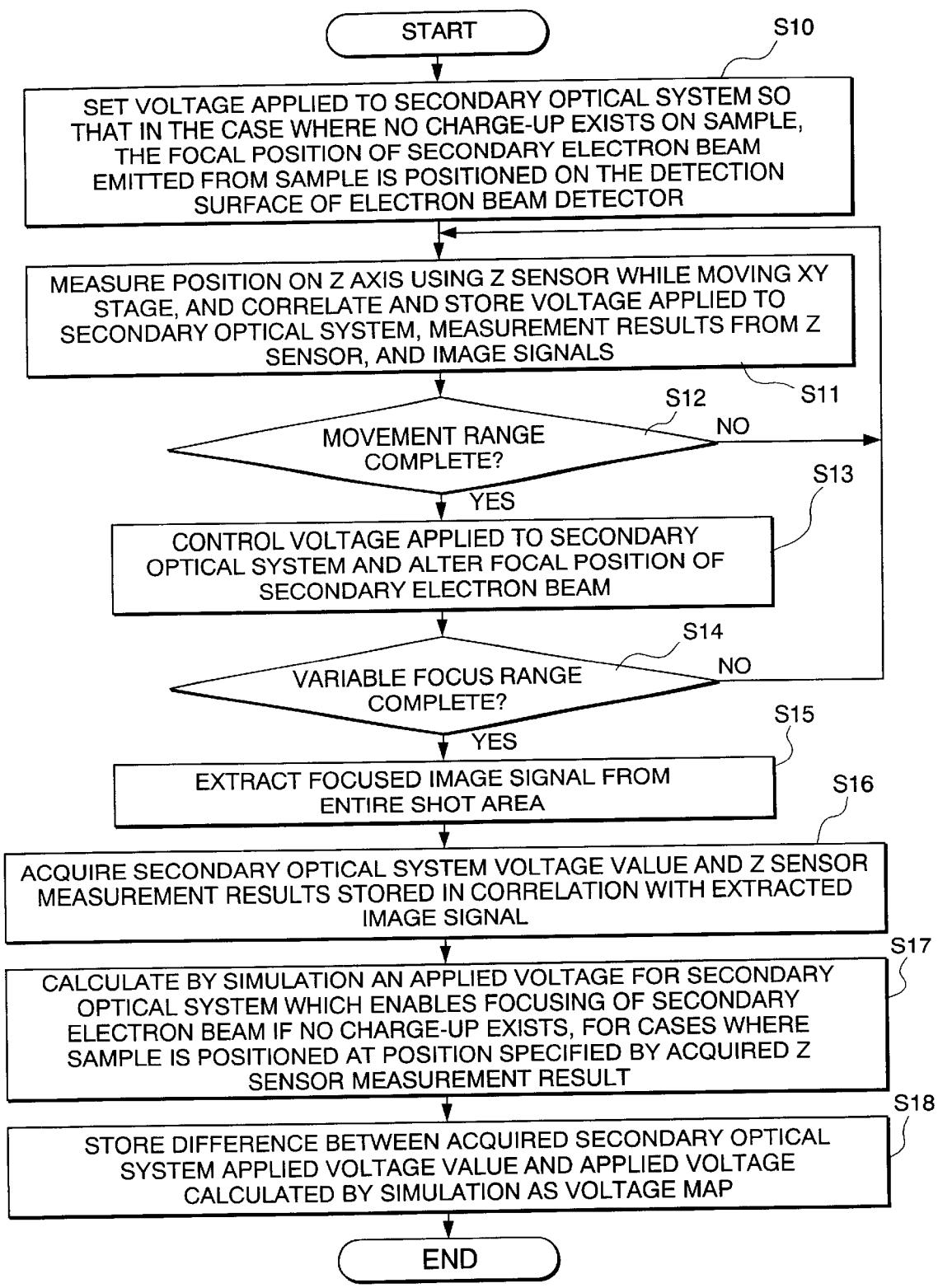
FIG. 9 is a flowchart showing a second method of preparing a voltage map.

A second method of preparing a voltage map described below, is a voltage map preparation method for those cases where a charged particle beam defect detection apparatus is not equipped with a Z stage, and therefore it is unable to vary the position of the sample 4 along the Z axis. FIG. 9 is a flowchart showing the second method of preparing a voltage map. On commencement of the voltage map preparation, first the position of the sample 4 within the XY plane and the magnification of the secondary optical system 20 are set so that the measurement range falls within one shot area, and a predetermined negative voltage is then applied to the sample 4 as part of the preparation for preparing the voltage map.

Next, the main control system 34 sets the voltage applied to the secondary optical system 20 so that the secondary electron beam B2 emitted from the sample 4 is imaged onto the detection surface of the electron beam detector 30 for the case where no charge-up is deemed to exist on the sample 4 (step S10). After completion of this setting process, the main control system 34 moves the sample 4 within the XY plane by driving the XY stage 38 via the drive apparatus 41, while using the Z sensor comprising the light transmission system 37a and the light reception system 37b to measure the position of the sample 4 on the Z axis. The main control system 34 then correlates the voltage applied to the secondary optical system 20, the position of the sample 4 on the Z axis as measured by the Z sensor, and the image signal input into the main control system 34 from the imaging element 32 via the control unit 33, and stores all the information in the storage device 43 (step S11).

Next, the main control system 34 determines whether or not movement processing has been completed for the entire movement range of the sample 4 (step S12). The movement range of the sample 4 is set as a single shot region, for example, in the case where a plurality of shot areas are formed on the object surface 4a of the sample 4 (refer to FIG. 4). In the case where the judgement is made that movement has not yet been performed across the entire movement range (that is, when the judgement result at step S12 is "NO"), the process returns to step S11, and the movement of the sample is continued, while the position of the 14 in the Z direction is measured by the Z sensor, and the processing is repeated for correlating the voltage applied to the secondary optical system 20, the position of the sample 4 on the Z axis, and the image signal, and storing the information in the storage device 43.

In contrast, in the case where the judgement is made that movement processing has been performed across the entire set movement range (that is, when the judgement result at step S12 is "YES"), the main control system 34 controls the voltage applied to the secondary optical system 20 and alters the focal position of the secondary electron beam B2 (step S13). The amount by which the focal position of the secondary electron beam B2 is altered is determined by using simulation to determine the focal depth of the secondary optical system 20 in advance, and then setting the alteration amount in accordance with this determined focal depth. In this second method of preparing a voltage map, adjustment of the focal position of the secondary electron beam B2 is performed by controlling the voltages applied to the front imaging lenses 25 and the rear imaging lenses 28 of FIG. 1, as well as the voltage and the current applied to the E×B 23.

When the focal position of the secondary electron beam B2 is altered, a judgement is made as to whether or not the processing for varying the predetermined focus through the entire variable range has been completed (step S14). In the case where the judgement is made that part of the focus variable range still remains (that is, when the judgement result at step S14 is "YES"), the process returns to step S11, and the processing described above is repeated. In those cases where the process returns from step S14 to step S11, then because the focal position of the secondary electron beam B2 has been altered at step S13, the value of the voltage applied to the secondary optical system 20 for storage in the storage device 43 at step S11 will change to a different value. If the judgement is made at step S14 that the processing has been completed for varying the predetermined focus through the entire variable range (that is, the judgement result at step S14 is "NO"), the process proceeds to step S15.

At step S15, the main control system 34 applies signal processing to the image signals stored in the storage device 43 by the processing outlined above, and performs processing for extracting a focused image signal for the entire shot area. As part of this processing, a judgement is made, based on the signal contrast for example, as to whether or not the image is focused. Then, the main control system 34 acquires the stored voltage value for the secondary optical system 20 and the stored Z sensor measurement results which correspond with the extracted image signal (step S16).

Subsequently, in the case where the sample 4 is positioned at the location shown by the Z sensor measurement results acquired at step S16, the main control system 34 calculates, by simulation, the voltage to apply to the secondary optical system 20 which will enable the secondary electron beam B2 to be focused onto the detection surface of the electron beam detector 30, assuming that no charge-up exists on the sample 4 (step S17). Then, the difference between the voltage for application to the secondary optical system 20 which is stored in correlation with the focused image signal as a result of the processing of step S16, and the voltage for application calculated by the simulation of step S17, is stored in the storage device 43 as a voltage map (step S18).

By carrying out the processing described above, the focal position deviation due to a positional deviation of the sample 4 along the Z axis, and the focal position deviation due to charge-up occurring on the sample 4 can be separated. Therefore, a voltage map can be prepared for correcting the focal position deviation corresponding with the amount of charge-up on the sample 4. A voltage map prepared in this manner can be used in cases where a charged particle beam defect detection apparatus such as that shown in FIG. 1 is not equipped with a Z stage for moving the sample 4 along the Z axis.

Third Method of Preparing a Voltage Map

The second method of preparing voltage map described above is used in cases where the charged particle beam defect detection apparatus is not equipped with a Z stage, and the focal position of the secondary electron beam B2 is controlled by controlling the voltage applied to the secondary optical system 20. A third method of preparing a voltage map is similar to the second method of preparing voltage map in terms of being used for charged particle beam defect detection apparatus not equipped with a Z stage, but differs in that the focal position of the secondary electron beam B2 is varied and a voltage map is prepared by controlling the variable power supply 42 and varying the negative voltage applied to the sample 4. As follows is a description of this third method of preparing a voltage map.

FIG. 10 is a flowchart showing the third method of preparing a voltage map. On commencement of the voltage map preparation, the position of the sample 4 within the XY plane and the magnification of the secondary optical system 20 are set so that the measurement range falls within one shot area, as part of the preparation for preparing the voltage map. Next, the main control system 34 sets the voltage applied to the sample 4 for the case where no charge-up is deemed to exist on the sample 4 (step S20). The main control system 34 then moves the sample 4 within the XY plane by driving the XY stage 38 via the drive apparatus 41, while using the Z sensor comprising the light transmission system 37a and the light reception system 37b to measure the position of the sample 4 on the Z axis.

Next, the main control system 34 applies a voltage to the secondary optical system 20 which is capable of focusing the secondary electron beam B2 onto the detection surface of the electron beam detector 30 in the case where no charge-up is deemed to exist on the sample 4 and when the sample 4 is positioned at the position measured by the Z sensor, thereby setting the focal position of the secondary electron beam (step S21). This process is performed to remove the effects of focal position deviations due to positional deviations of the sample 4 along the Z axis. However even if this process is performed, because charge-up may occur on the sample 4, the focal position of the secondary optical system 20 may not necessarily be positioned on the detection surface of the electron beam detector 30.

Subsequently, the main control system 34 correlates the voltage applied to the sample 4 with the image signal input into the main control system 34 from the imaging element 32 via the control unit 33, and stores the correlated information in the storage device 43 (step S22). After completion of the processing of step S22, the main control system 34 determines whether or not movement processing has been completed for the entire movement range of the sample 4 (step S23). The movement range of the sample 4 is set as a single shot region, for example, in the case where a plurality of shot areas are formed on the object surface 4a of the sample 4 (refer to FIG. 4). In the case where the judgement is made that movement has not yet been performed across the entire movement range (that is, when the judgement result at step S23 is "NO"), the process returns to step S21, and the above processing is repeated.

In contrast, in the case where the judgement is made that movement processing has been performed across the entire set movement range (that is, when the judgement result at step S23 is "YES"), the main control system 34 controls the variable power supply 42, marginally altering the voltage applied to the sample 4 and altering the focal position of the secondary electron beam B2 (step S24). In the second method of preparing voltage map described above, the focal position of the secondary electron beam B2 was varied by controlling the voltage applied to the secondary optical system 20, and satisfying the Wien's condition in the E×B 23 requires the controlling of the voltages applied to the front imaging lenses 25 and the rear imaging lenses 28 of FIG. 1, as well as the voltage and the current applied to the E×B 23. In contrast, in the processing of step S24, the focal position of the secondary electron beam B2 is varied by altering the voltage applied to the sample 4, and so the Wien's condition in the E×B 23 can be satisfied without requiring control of the voltage and current applied to the E×B 23, thereby simplifying the control process.

When the focal position of the secondary electron beam B2 has been altered by controlling the voltage applied to the sample 4, a judgement is made as to whether or not the processing for varying the predetermined voltage through the entire variable range has been completed (step S25). In the case where the judgement is made that part of the focus variable range still remains (that is, when the judgement result at step S25 is "YES"), the process returns to step S21, and the processing described above is repeated. In those cases where the process returns from step S25 to step S21, then because the voltage applied to the sample 4 has been altered at step S24, the value of the voltage applied to the sample 4 for storage in the storage device 43 at step S22 will change to a different value. If the judgement is made at step S25 that the processing has been completed for varying the predetermined voltage through the entire variable range (that is, the judgement result at step S25 is "NO"), the process proceeds to step S26.

At step S26, the main control system 34 applies signal processing to the image signals stored in the storage device 43 by the processing outlined above, and performs processing for extracting a focused image signal for the entire shot area. As part of this processing, a judgement is made, based on the signal contrast for example, as to whether or not the image is focused, in the same manner as the second method of preparing a voltage map. Then, the main control system 34 acquires the stored voltage value for application to the sample 4 which correspond with the extracted image signal (step S27). The difference between the applied voltage value for the sample 4 acquired at this point, and the applied voltage value for the sample 4 in the case where no charge-up occurs on the sample 4 is stored in the storage device 43 as a voltage map (step S28).

By carrying out the processing described above, the focal position deviation due to a positional deviation of the sample 4 along the Z axis, and the focal position deviation due to charge-up occurring on the sample 4 can be separated. Therefore, a voltage map can be prepared for correcting the focal position deviation corresponding with the amount of charge-up on the sample 4. A voltage map prepared in this manner can be used in cases where a charged particle beam defect detection apparatus such as that shown in FIG. 1 is not equipped with a Z stage for moving the sample 4 along the Z axis. The above descriptions detail methods of preparing voltage maps, and as follows is a description of the operation for using such voltage maps for correcting focal position deviations in the secondary electron beam B2 resulting from charge-up on the sample 4.

Focal Position Correction Using a Voltage Map Prepared by the First Preparation Method First, the position of the sample 4 within the XY plane and the magnification of the secondary optical system 20 are set so that the measurement range falls within one shot area, and a predetermined negative voltage is then applied to the sample 4. The position of the sample 4 on the Z axis is then measured using the Z sensor comprising the light transmission system 37a and the light reception system 37b. Based on the measurement result, the main control system 34 uses the drive apparatus 41 to drive the Z stage and position the sample 4 at a predetermined Z position.

After positioning of the sample 4 at this predetermined Z position, the main control system 34 adjusts the voltage applied to the secondary optical system 20 so that the secondary electron beam B2 emitted from the sample 4 is imaged onto the detection surface of the electron beam detector 30 for the case where no charge-up is deemed to exist on the sample 4. The main control system 34 then reads the voltage map stored in the storage device 43, and based on this voltage map, adjusts the voltage applied to the secondary optical system 20, thereby positioning the focal position of the secondary electron beam B2 onto the detection surface of the electron beam detector 30 and creating a focused image of the secondary electron beam B2 on the detection surface.

Focal Position Correction Using a Voltage Map Prepared by the Second Preparation Method First, in the same manner as the case described above where correction was performed using a voltage map prepared by the first preparation method, the position of the sample 4 within the XY plane and the magnification of the secondary optical system 20 are set so that the measurement range falls within one shot area, and a predetermined negative voltage is applied to the sample 4. The position of the sample 4 on the Z axis is then measured using the Z sensor comprising the light transmission system 37a and the light reception system 37b. Based on the measurement result, the main control system 34 sets the voltage applied to the secondary optical system 20 so that the secondary electron beam B2 is imaged onto the detection surface of the electron beam detector 30 for the case where no charge-up is deemed to exist on the sample 4.

The main control system 34 then reads the voltage map stored in the storage device 43, and adjusts the voltage applied to the secondary optical system 20, thereby positioning the focal position of the secondary electron beam B2 onto the detection surface of the electron beam detector 30 and creating a focused image of the secondary electron beam B2 on the detection surface. In those cases where a voltage map prepared by the aforementioned first preparation method or second preparation method are used for correcting the focal position, the initial energy of the secondary electron beam B2 increases by the amount of charge-up, and because the Wien's condition is not satisfied within the E×B 23, the main control system 34 needs to control the voltages applied to the front imaging lenses 25 and the rear imaging lenses 28, as well as the voltage and the current applied to the E×B 23.

Focal Position Correction Using a Voltage Map Prepared by the Third Preparation Method First, the position of the sample 4 within the XY plane and the magnification of the secondary optical system 20 are set so that the measurement range falls within one shot area, and the position of the sample 4 on the Z axis is then measured by the Z sensor. Then, the main control system 34 applies a voltage to the secondary optical system 20 which is capable of focusing the secondary electron beam B2 onto the detection surface of the electron beam detector 30 in the case where no charge-up is deemed to exist on the sample 4 and when the sample 4 is positioned at the position measured by the Z sensor, thereby setting the focal position of the secondary electron beam.

Subsequently, the main control system 34 reads the voltage map stored in the storage device 43 and corrects the focal position of the secondary electron beam B2 by applying to the sample 4, a voltage equivalent to the voltage applied to the sample 4 in the case where no charge-up occurs corrected by the voltage map value read from the storage device 43. In the case where a voltage map prepared by the third preparation method is used for correcting the focal position, the initial energy of the secondary electron beam B2 emitted from the sample 4 is adjusted by correcting the voltage applied to the sample 4, thereby correcting the focal position of the secondary electron beam B2. Therefore, the Wien's condition is satisfied in the E×B 23, and so the control process can be simplified. When shot areas outside the observed shot area are to undergo observation, the voltage maps prepared by any one of the first, second and third preparation methods described above can be used for adjusting the focal position and conducting the observation.

A charged particle beam defect detection apparatus according to one embodiment of the present invention has been described above, but the present invention is in no way limited to the aforementioned embodiment, and various modifications are possible within the scope of the present invention. For example, in the first method of preparing a voltage map described above, the voltage map was prepared and the focal position of the secondary electron beam B2 corrected by controlling the voltage applied to the secondary optical system 20, but a voltage map could also be prepared relating to the voltage applied to the sample 4. Furthermore, the description of the above embodiment outlined the case where a plurality of shot areas were set on the surface of a sample 4 and a voltage map was then generated for one of the shot areas, but in the case of low magnification observations, a voltage map could be prepared by using an average value of the charge-up on the sample 4 for the charge-up value across the entire sample 4, and the focal position could then be corrected based on this voltage map.

Furthermore, in the aforementioned embodiment, the situation was described where an E×B 23 was used for deflecting and irradiating the primary electron beam B1 onto the sample 4 and allowing the secondary electron beam B2 generated at the sample 4 to travel straight through. However, the present invention is not limited to this type of construction, and for example an electromagnetic prism which allows the primary electron beam B1 to travel straight through and deflects the secondary electron beam B2 could also be used. Furthermore, in the embodiment described above, a charged particle beam imaging projection optical system using an electron beam was shown, but a charged particle beam imaging projection optical system using an ion beam instead of an electron beam is also possible. In addition, the charged particle beam imaging projection optical system of the above embodiment is a so-called surface to surface charged particle beam imaging projection optical system, using an electron beam from a beam source to irradiate the object surface of a sample and project an image onto an imaging surface, and as such is not limited to the simple observation and detection apparatus described above, but can also be easily applied to other devices such as semiconductor exposure apparatus. Moreover, the description of the above embodiment focused on the correction of focal position deviations resulting from accumulated charge on the object, but by measuring the surface voltage distribution of the object, the data could also be used for the analysis and correction of image distortion.

What is claimed is:

1. A charged particle beam defect detection apparatus comprising:
   an irradiation device which irradiates a beam from a charged particle beam source as a primary beam onto an object;
   an electron detection device which detects electrons emitted from said object as a result of said primary beam irradiation as a secondary beam, and captures an image of said object; and
   an detection device which detects a surface voltage distribution for said object corresponding with an amount of accumulated charge generated on said object upon irradiation with said primary beam.

2. A charged particle beam defect detection apparatus comprising:
   an irradiation device which irradiates a beam from a charged particle beam source as a primary beam onto an object;
   an electron detection device which detects electrons emitted from said object as a result of said primary beam irradiation as a secondary beam, and captures an image of said object;
   a focus deviation detection device which detects in advance a degree of focus deviation of said secondary beam at a detection surface of said electron detection device which corresponds with an amount of accumulated charge generated on said object upon irradiation with said primary beam; and
   a focus control device which controls a focal position of said secondary beam in accordance with said degree of focus deviation detected by said focus deviation detection device.

3. A charged particle beam defect detection apparatus according to claim 2, further comprising a storage device which stores focus deviation values detected by said focus deviation detection device, wherein
   said focus control device controls a focal position of said secondary beam based on said focus deviation values stored in said storage device.

4. A charged particle beam defect detection apparatus according to claim 2, further comprising a height detection device which detects a height of said object, wherein
   said focus control device controls a focal position of said secondary beam based on both said focus deviation values, and detection results from said height detection device.

5. A charged particle beam defect detection apparatus according to claim 4, wherein
   said storage device stores said object height values detected by said height detection device in correlation with corresponding focus detection values, and
   said focus control device controls a focal position of said secondary beam based on both said focus deviation values and said object height values correlated by said storage device.

6. A charged particle beam defect detection apparatus according to claim 2, further comprising an imaging electron optical system which is provided between said electron detection device and said object and images said secondary beam onto a detection surface of said electron detection device, wherein
   said focus control device controls a focal position of said secondary beam by controlling said imaging electron optical system.

7. A charged particle beam defect detection apparatus according to claim 2, further comprising a voltage application device which applies a predetermined voltage to said object, wherein
   said focus control device controls a focal position of said secondary beam by controlling a voltage applied to said object via said voltage application device.

8. A charged particle beam defect detection apparatus according to claim 7, wherein
   said focus control device controls a focal position of said secondary beam by controlling a voltage applied to said object based on focus deviation values stored in said storage device.

9. A charged particle beam defect detection apparatus according to claim 2, further comprising:
   a height detection device which detects a height of said object;
   an imaging electron optical system which is provided between said electron detection device and said object and images said secondary beam onto a detection surface of said electron detection device; and
   a focused position calculation device which determines, by simulation, a relationship between height of said object, and a focused position of said imaging electron optical system relative to a detection surface of said electron detection device, for those cases where no accumulated charge exists on said object, wherein
   said focus deviation detection device varies a focal position of said imaging electron optical system and saves object height values detected by said height detection device together with imaging results from said electron detection device, and based on a difference between a focal position of said imaging electron optical system at a saved height value corresponding with a focused imaging result, and a focused position of said imaging electron optical system corresponding with said height value as determined by said focused position calculation device, determines an amount of focus deviation of said secondary beam at a detection surface of said electron detection device corresponding with said amount of accumulated charge.

10. A charged particle beam defect detection apparatus according to claim 2, further comprising:
    a voltage application device which applies a predetermined voltage to said object;
    a height detection device which detects a height of said object;
    an imaging electron optical system which is provided between said electron detection device and said object and images said secondary beam onto a detection surface of said electron detection device; and
    a focused position calculation device which determines, by simulation, a relationship between height of said object, and a focused position of said imaging electron optical system relative to a detection surface of said electron detection device for those cases where no accumulated charge exists on said object; wherein
    said focus deviation detection device varies a voltage applied to said object via said voltage application device and saves imaging results from said electron detection device when a focal position of said imaging electron optical system is matched with a focused position as determined by said focused position calculation device in accordance with height values obtained by said height detection device, and based on an amount of variation in voltage applied to said body in a case where a focused imaging result is obtained, determines an amount of focus deviation in said secondary beam at a detection surface of said electron detection device corresponding with said amount of accumulated charge.

11. A charged particle beam defect detection method comprising:

irradiating a beam from a charged particle beam source as a primary beam onto an object, and detecting defects by detecting electrons emitted from said object as a secondary beam and capturing an image of said object, wherein an amount of focus deviation of said secondary beam corresponding with an amount of accumulated charge generated on said object upon irradiation with said primary beam is detected in advance, and a focal position of said secondary electron beam is controlled in accordance with said detected amount of focus deviation.

* * * * *